United States Patent
Jackson et al.

(10) Patent No.: US 8,961,727 B2
(45) Date of Patent: Feb. 24, 2015

(54) APPARATUS AND METHODS FOR THE OPTICAL EXAMINATION OF BIREFRINGENT SPECIMENS

(75) Inventors: Andrew Robert William Jackson, Stoke-on-Trent (GB); Claire Margaret Betty Gwinnett, West Midlands (GB)

(73) Assignee: Staffordshire University, Stafford (GB)

( * ) Notice: Subject to any disclaimer, the term of this patent is extended or adjusted under 35 U.S.C. 154(b) by 567 days.

(21) Appl. No.: 13/382,208

(22) PCT Filed: Jul. 1, 2010

(86) PCT No.: PCT/GB2010/001274
§ 371 (c)(1),
(2), (4) Date: Mar. 26, 2012

(87) PCT Pub. No.: WO2011/004139
PCT Pub. Date: Jan. 13, 2011

(65) Prior Publication Data
US 2012/0176617 A1    Jul. 12, 2012

(30) Foreign Application Priority Data
Jul. 6, 2009  (GB) .................................. 0911706.0

(51) Int. Cl.
*B29C 65/50* (2006.01)
*B32B 37/14* (2006.01)
(Continued)

(52) U.S. Cl.
CPC ................ *G01N 21/23* (2013.01); *B01L 3/505* (2013.01); *G02B 21/34* (2013.01);
(Continued)

(58) Field of Classification Search
CPC ........ G01N 21/23; G02B 21/34; B01L 3/505; B01L 2200/141; B01L 2300/044; B01L 2300/0822; B01L 2300/0887; B01L 21/6835; B32B 7/06; B32B 37/12; B32B 38/10

USPC .................................................. 156/247, 249
See application file for complete search history.

(56) References Cited

U.S. PATENT DOCUMENTS 4,544,583 A * 10/1985 Claussen et al. ................ 428/1.5
5,677,024 A   10/1997 Abe et al.
(Continued)

FOREIGN PATENT DOCUMENTS

WO         03010569       2/2003
WO        2006038023      4/2006

OTHER PUBLICATIONS

Rogers, R.N. & Arnoldi, A., Scientific Method Applied to the Shroud of Turin, 2002, pp. 1-38.
Teetsov, A.S., Hand-Sectioning and Identification of Pressure-Sensitive Tapes, Modern Microscopy Journal, 2004, p. 21.
(Continued)

*Primary Examiner* — Sing P Chan
(74) *Attorney, Agent, or Firm* — Kirschstein, et al.

(57) ABSTRACT

A method for optically examining a birefringent specimen, the method comprising the steps of: collecting a specimen using a substantially non-birefringent polymer film having an adhesive surface, such that the specimen is attached to the adhesive surface; and examining, between crossed polars, the specimen attached to the said film. Also provided is a substantially non-birefringent laminate film comprising: a first birefringent polymer layer and a second birefringent polymer layer, the first and second layers being mutually oriented such that the birefringent properties of the two layers cancel each other out; and an adhesive surface; wherein the adhesive surface is an outer surface of the film, and/or is an exposable surface between the first and second layers. A method of manufacturing such a film is also provided.

10 Claims, 15 Drawing Sheets

(51) Int. Cl.
  *B32B 38/10* (2006.01)
  *G01N 21/23* (2006.01)
  *B01L 3/00* (2006.01)
  *G02B 21/34* (2006.01)

(52) U.S. Cl.
  CPC ..... *B01L 2200/141* (2013.01); *B01L 2300/044* (2013.01); *B01L 2300/0822* (2013.01); *B01L 2300/0887* (2013.01)
  USPC .......................................... 156/247; 156/249

(56) References Cited

U.S. PATENT DOCUMENTS

| | | |
|---|---|---|
| 5,888,603 A | 3/1999 | Fergason |
| 5,905,554 A | 5/1999 | Kyu |
| 2002/0145804 A1 | 10/2002 | Yano et al. |

OTHER PUBLICATIONS

Kiernan, J.A., Making and Using Acqueous Mounting Media, 1997, p. 1, IHC World Protocols.

* cited by examiner

| Fibre 5 over Depex | |
|---|---|
| Position | OPD |
| 1 | 73.3 |
| 2 | 67.9625 |
| 3 | 68.3 |
| 4 | 64.25 |
| 5 | 65.6 |
| 6 | 68.3 |
| 7 | 74.375 |
| 8 | 71.2 |
| 9 | 68.6625 |
| 10 | 70.8375 |
| 11 | 68.6625 |
| 12 | 65.9375 |
| 13 | 71.2 |
| 14 | 65.6 |
| 15 | 67.2875 |
| 16 | 65.2625 |
| 17 | 70.475 |
| 18 | 70.475 |
| 19 | 69.025 |
| Mean | 68.77434 |
| SD | 2.769563 |

| Fibre 5 over J-LAR | |
|---|---|
| Angle | OPD |
| | |
| | |
| 17.8 | 108.15 |
| 25.3 | 76.75 |
| 35.5 | 98.801 |
| 47.3 | 151.075 |
| 60.8 | 140.9 |
| 69.1 | 163.725 |
| 78.2 | 189.975 |
| 90.3 | 189.975 |
| 98.9 | 183.65 |
| 112.8 | 161.0375 |
| 124.2 | 146.975 |
| 129.9 | 135.425 |
| 138.5 | 131.6125 |
| 152.8 | 66.6125 |
| 162.4 | 51.4 |
| 170.5 | 50.2 |
| | |
| Mean | 127.8915 |
| SD | 47.49412 |

Figure 8

| Fibre 5 over New Tape ||
|---|---|
| Angle | OPD |
| 0 | 77.875 |
| 11.9 | 66.275 |
| 18.7 | 63.575 |
| 30.8 | 54.7875 |
| 38.9 | 66.275 |
| 51.6 | 63.2375 |
| 59.3 | 54.1625 |
| 69.5 | 55.725 |
| 79.7 | 61.55 |
| 89.9 | 56.6625 |
| 99.5 | 62.9 |
| 110.7 | 56.35 |
| 119.9 | 58.9 |
| 131.4 | 57.925 |
| 137.4 | 56.975 |
| 150.6 | 56.6625 |
| 160.2 | 65.6 |
| 169.6 | 63.575 |
| 180 | 69.025 |
| Mean | 61.47566 |
| SD | 5.992345 |

| Fibre 5 over Gelatine ||
|---|---|
| Angle | OPD |
| 0 | 72.4 |
| 13.8 | 76.375 |
| 22.3 | 76 |
| 32.7 | 79 |
| 39.4 | 74.875 |
| 50.6 | 75.625 |
| 58.8 | 84.275 |
| 69.7 | 77.875 |
| 76.3 | 75.625 |
| 88.2 | 73.45 |
| 96.8 | 82.375 |
| 110.6 | 79 |
| 124 | 82 |
| 135.3 | 74.875 |
| 144.6 | 76.75 |
| 147.8 | 83.125 |
| 155.8 | 78.25 |
| 166.8 | 76 |
| 180 | 79.75 |
| Mean | 77.76974 |
| SD | 3.333277 |

Figure 8 (continued)

| Fibre 5 over Gelatine and New Tape ||
|---|---|
| Angle | OPD |
| 0 | 76.375 |
| 11.9 | 75.625 |
| 22.5 | 81.25 |
| 31.1 | 82 |
| 42.3 | 79 |
| 50.4 | 69.3875 |
| 62.5 | 70.1125 |
| 70.6 | 70.1125 |
| 77.9 | 77.5 |
| 88.2 | 65.5 |
| 97.6 | 65.875 |
| 113.6 | 61 |
| 120.1 | 69.75 |
| 128.5 | 71.7 |
| 135.8 | 73.8 |
| 148.5 | 80.875 |
| 159.2 | 90.2 |
| 168.5 | 86.2125 |
| 180 | 68.6625 |
| Mean | 74.47039 |
| SD | 7.554939 |

Figure 8 (continued)

| Fibre 123 over Depex | |
|---|---|
| Position | OPD |
| 1 | 847.5875 |
| 2 | 819.9 |
| 3 | 858.5 |
| 4 | 828.3 |
| 5 | 818.7125 |
| 6 | 830.7 |
| 7 | 835.5 |
| 8 | 846.375 |
| 9 | 804.4625 |
| 10 | 867.075 |
| 11 | 819.9 |
| 12 | 827.1 |
| 13 | 819.9 |
| 14 | 854.8625 |
| 15 | 807.575 |
| 16 | 843.95 |
| 17 | 841.525 |
| 18 | 819.9 |
| 19 | 850.0125 |
| 20 | 819.9 |
| Mean | 833.0869 |
| SD | 17.40282 |

| Fibre 123 over J-LAR | |
|---|---|
| Angle | OPD |
| 0 | 919.375 |
| 9.6 | 850.0125 |
| 21.7 | 904.35 |
| 31.4 | 827.1 |
| 42.4 | 829.5 |
| 51.6 | 753.25 |
| 59.1 | 767.05 |
| 71.1 | 724.85 |
| 79.8 | 713.65 |
| 91.3 | 731.6 |
| 97.8 | 691.325 |
| 111.3 | 730.475 |
| 119.7 | 693.7 |
| 132.4 | 749.8 |
| 137.8 | 756.7 |
| 148.6 | 813.9625 |
| 159.2 | 880.675 |
| 167.5 | 919.375 |
| 180 | 904.35 |
| | |
| Mean | 797.9526 |
| SD | 79.72194 |

Figure 9

| Fibre 123 over New Tape ||
|---|---|
| Angle | OPD |
| 0 | 789.15 |
| 10.5 | 857.53 |
| 17.4 | 835.5 |
| 29.4 | 833.1 |
| 40.4 | 837.9 |
| 51.3 | 828.3 |
| 60.9 | 815.15 |
| 68.6 | 830.7 |
| 77.3 | 839.1 |
| 90.1 | 823.5 |
| 99.7 | 847.5875 |
| 111.4 | 828.3 |
| 121.3 | 846.375 |
| 129.4 | 829.5 |
| 142.5 | 804.4625 |
| 147.8 | 766.95 |
| 159.8 | 837.9 |
| 171.2 | 835.5 |
| 180 | 827.1 |
| Mean | 827.031842 |
| SD | 21.1076656 |

| Fibre 123 over Gelatine and New Tape ||
|---|---|
| Angle | OPD |
| 38.6 | 859.725 |
| 50.4 | 842.7375 |
| 69.1 | 881.9125 |
| 88.5 | 839.1 |
| 108.7 | 847.5875 |
| 132.1 | 872.0125 |
| 143.2 | 851.225 |
| Mean | 856.3286 |
| SD | 15.79057 |

Figure 9 (continued)

APPARATUS AND METHODS FOR THE OPTICAL EXAMINATION OF BIREFRINGENT SPECIMENS

This invention relates, in part, to methods for the optical examination of birefringent specimens. These methods are particularly applicable, but by no means limited, to the forensic analysis of fibres found at crime scenes. Other applications include the examination of specimens in various fields of scientific or technological research. This invention also relates, in part, to apparatus that may be used in such applications, although a wider range of industrial applications are also possible.

BACKGROUND TO THE INVENTION

In many fields of optical investigation of specimens, such as forensic analysis or in materials science, useful information can often be obtained from viewing a specimen between a pair of crossed polarizing filters (or "crossed polars" as they are known in the art) under a microscope, in order to observe any interference colours (also known as retardation colours) produced by the specimen if it is birefringent. As those skilled in the art will appreciate, when viewed between crossed polars a birefringent specimen often appears bright against a dark background, and typically exhibits a multicoloured pattern characteristic of the underlying composition and structure of the specimen. Many polymer materials are birefringent, because the polymer molecules are 'frozen' in a more-or-less parallel configuration when the plastic is extruded or moulded. Many crystalline materials are also birefringent, such as calcite, for example. Some fibres (e.g. as used in fabrics) are also birefringent. For example, cotton fibres are birefringent because of high levels of cellulosic material in the fibre's secondary cell wall. By observing a birefringent specimen between crossed polars and analysing the colours and patterns seen, the material can be characterised. For example, the pattern often indicates the manner in which a polymer material was extruded or moulded. Furthermore, if the thickness of the specimen is known, it is often possible to establish its birefringence from the interference colours that it exhibits between crossed polars. Thus, observation of these colours can be a particularly useful technique in forensic investigation (e.g. enabling fibre samples to be compared with one another, or linked to a clothing manufacturer or supplier), although it also has extensive applications in materials science and other fields of scientific and technological research.

By way of some background to forensic investigation techniques, it is relatively easy for a criminal to avoid leaving his or her fingermarks at a crime scene. Similarly, he or she can often guard against leaving detectable quantities of DNA behind when committing a crime. In contrast, it is virtually impossible for a criminal to be present at a crime scene without the two-way transfer of fibres occurring between the scene and the person concerned. This has meant that fibres evidence has been pivotal in solving a number of serious crimes, e.g. involving kidnapping, murder or rape. However, despite its advantages, in the main, fibres evidence is not routinely used in volume crime cases. This is for a number of reasons, one of which is the difficulty of examining fibres quickly, easily and cost-effectively, without risking contamination (which could cause the evidence to be rejected in court). The difficulty of examining fibres has also hampered the compilation of a suitable fibres database for forensic investigation purposes.

There are a number of means by which fibres evidence can be collected from crime scenes. These include brushing, scraping and vacuuming. However, the most common method in use is tape-lifting—a process that involves using an adhesive polymer tape (similar to Sellotape®) to remove fibres from the surface to be sampled. This tape is then adhered to a suitable backing sheet so as to capture the fibres between the tape and the sheet, packaged, and then sent to a laboratory for analysis of the fibres.

The fibres can be analysed by a range of techniques, including infra-red and Raman spectroscopy, pyrolysis-gas chromatography, and polarised-light microscopy. Of these, the technique that is most commonly used is polarised-light microscopy to observe interference colours and establish birefringence values, as it is highly discriminating and non-destructive. However, the conventional polymer tape that is used to collect the fibres evidence interferes with this technique, as the tape itself is birefringent too. As a consequence, to establish the fibres' birefringence, the fibres are individually dissected from the tape, removed, and then placed into a suitable mounting medium between a microscope slide and a cover slip. As a result of all these steps, and the need to use skilled personnel to conduct the examination with care such that the evidence will be properly admissible in court, the process is both time-consuming and expensive. Moreover, throughout the dissection and remounting process, there is a risk that the fibres could be lost or contaminated, which would render them useless as evidence in court, and could potentially affect the outcome of a case.

Accordingly there is a need for a quicker, easier and reliable process for capturing birefringent fibres or other such materials and examining the interference colours that they exhibit when illuminated between crossed polars. There is also a desire for a tape or film that does not meaningfully alter such colours produced by a birefringent specimen such as a fibre captured thereon.

Background art is provided in WO 03/010569 A2, WO 2006/038023 A1, U.S. Pat. No. 5,677,024 and U.S. Pat. No. 4,544,583. WO 03/010569 A2 discloses an optical filter. WO 2006/038023 A1 discloses a sample-lifting tape and a method for the collection of a sample from an area, for example for forensic examination. U.S. Pat. No. 5,677,024 discloses a laminate having particular polarisation characteristics, and U.S. Pat. No. 4,544,583 discloses a birefringence-free arrangement of plastic foils.

SUMMARY OF THE INVENTION

According to a first aspect of the present invention there is provided a method as defined in claim 1 of the appended claims. Thus there is provided a method for optically examining a birefringent specimen, the method comprising the steps of: collecting a specimen using a substantially non-birefringent polymer film having an adhesive surface, such that the specimen is attached to the adhesive surface; and examining, between crossed polars, the specimen attached to the said film.

The term "substantially non-birefringent" as used herein should be interpreted broadly, to encompass a film that appears black or very dark when viewed between crossed polars, and also a film that appears significantly less bright than a birefringent specimen attached thereto.

The term "film" as used herein should be interpreted broadly, to encompass materials supplied in continuous (e.g. tape) form, and also materials supplied in discontinuous form, for example as individual squares, rectangles or other shapes, with or without a backing layer.

The term "adhesive surface" and variations thereof should also be interpreted broadly, to encompass an entire surface that is sticky or coated with adhesive, and also surfaces that are only partly sticky or partly coated with adhesive.

By collecting the specimen using a substantially non-birefringent polymer film having an adhesive surface, this avoids the need for the dissection, removal and slide-making steps associated with the prior art tape-lift technique, since the film and specimen can be directly viewed between crossed polars without the film meaningfully altering the interference colours observed. This thereby expedites and facilitates the examination of the specimen, and reduces the risk of losing or contaminating it.

Preferable, optional, features are defined in the dependent claims.

Thus, preferably the film has an adhesive underside, and the step of collecting the specimen is performed by placing the film onto the specimen such that the adhesive underside contacts the specimen, and then lifting the film up. This corresponds to the tape-lift technique known to forensic scientists and scene-of-crime officers.

Alternatively, the film may comprise two or more layers, and the step of collecting the specimen may be performed by peeling a layer at least partly away so as to expose an adhesive surface, collecting the specimen using the said adhesive surface, and closing the layers together again, so as to seal the specimen between the layers. This provides the further advantage that the specimen may be immediately sealed safely between the layers, thus further reducing the risk of contamination or loss of the specimen.

After collecting the specimen and before examining it between crossed polars, the method may further comprise attaching the film to a substantially non-birefringent substrate (sandwiching the specimen between the film and the substrate if the specimen is attached to an outer surface of the film). This facilitates the handling, labelling and storage of the film and specimen. The substrate may be a glass slide, or another material having similar optical properties.

Preferably a surface of the substrate comprises a coating of gelatine, or another material having similar optical and viscous properties to gelatine, onto which the film is attached. The presence of the gelatine causes fewer air bubbles to form between the film and the substrate, and thereby improves the subsequent imaging of the specimen.

In order to improve the seal between the film and the substrate, the method may further comprise applying heat and pressure to the substrate, with the film and specimen attached, before examining the specimen between crossed polars. In a presently-preferred embodiment, the application of heat and pressure comprises placing the substrate, with the film and specimen attached, between two layers of paper (e.g. inside a piece of folded paper), and passing it through a conventional office laminating machine. The method may yet further comprise placing a weight on the substrate, with the film and specimen attached, after it has passed through the laminating machine.

The method may further comprise an initial step of removing a layer of backing material from the film prior to collecting the specimen.

The substantially non-birefringent film may be a laminate film according to a second aspect of the present invention, as discussed below.

The specimen may be a piece of evidence such as a fibre from a crime scene, in which case the method may be for the forensic analysis of such evidence.

According to a second aspect of the present invention there is provided a substantially non-birefringent laminate film comprising: a first birefringent polymer layer and a second birefringent polymer layer, the first and second layers being mutually oriented such that the birefringent properties of the two layers cancel each other out; and an adhesive surface; wherein the adhesive surface is an outer surface of the film, and/or is an exposable surface between the first and second layers.

By virtue of the substantially non-birefringent nature of the film, it will not meaningfully alter the interference colours of a birefringent specimen, such as a fibre, captured thereon when it is illuminated between crossed polars. Consequently, this avoids the need to remove and remount the specimen prior to viewing it between crossed polars. Accordingly, time and expense may be saved, and there is less risk of contaminating or losing the specimen.

The adhesive surface facilitates the capture of specimens onto the film. If the adhesive surface is an outer surface of the film, this enables small specimens such as fibres to be picked up on the outside of the film, using a tape-lift technique known to forensic scientists and scene-of-crime officers. Alternatively, if the adhesive surface is an exposable surface between the first and second layers of the film, this provides the advantage that a specimen attached to this adhesive surface may be immediately sealed safely between the layers, thus reducing the risk of contamination or loss of the specimen.

The first and second layers preferably comprise adhesive polymer tape. Particularly preferably the second layer is oriented at substantially 90° relative to the first layer (i.e. such that the vibration direction of the slow beam of light passing through the second layer is oriented at substantially 90° relative to that of the slow beam of light passing through the first layer).

According to a third aspect of the present invention there is provided a method of manufacturing a substantially non-birefringent laminate film, the method comprising the steps of: adhering a second birefringent polymer layer on top of a first birefringent polymer layer, the first and second layers being mutually oriented such that the birefringent properties of the two layers cancel each other out; and providing an adhesive surface on an outer surface of the film and/or as an exposable surface between the first and second layers.

The method may further comprise manipulating the first and second layers between crossed polars to establish the mutual orientation at which the birefringent properties of the two layers cancel each other out.

The method may yet further comprise attaching the first layer to a piece of glass or optically similar material, prior to manipulating the first and second layers between the crossed polars.

Furthermore, to facilitate removal of the film from the glass without risking contamination of the adhesive surface of the film, the method may further comprise placing a piece of release paper/film between the piece of glass and the first layer of the film.

In a broad sense, the present invention provides a polymer film that is substantially non-birefringent. As noted above, the term "film" should be interpreted broadly, to encompass materials supplied in continuous (e.g. tape) form, and also materials supplied in discontinuous form, for example as individual squares, rectangles or other shapes, with or without a backing layer.

BRIEF DESCRIPTION OF THE DRAWINGS

Embodiments of the invention will now be described, by way of example only, and with reference to the drawings in which:

FIG. 8 comprises a series of tables of observational results made on a fibre (so-called "Fibre 5") using a tilting compensator; and FIG. 9 comprises another series of tables of observational results made on another fibre (so-called "Fibre 123");

In the figures, like elements are indicated by like reference numerals throughout. FIGS. 1 to 7 are not drawn to scale. In particular, in the interest of clarity, the thickness of the layers and films has been greatly exaggerated. As those skilled in the art will appreciate, the shapes and sizes of the elements depicted may vary widely in practice, to suit the intended purpose. Similarly, any dimensions mentioned herein should be regarded merely as examples, as a wide range of values are possible in practice.

DETAILED DESCRIPTION OF PREFERRED EMBODIMENTS

The present embodiments represent the best ways known to the applicants of putting the invention into practice. However, they are not the only ways in which this can be achieved.

Although the embodiments herein will principally be described in the context of forensic science, it is to be understood that they are more widely applicable, such as for the examination of birefringent specimens in various fields of scientific or technological research, or for other industrial applications.

One aspect of the present disclosure provides a simplified technique for the capture and analysis of birefringent specimens between crossed polars. This technique involves the use of an adhesive transparent polymer film that is substantially non-birefringent. We have devised such a film, which forms another aspect of the present disclosure. We will first discuss this film and its method of manufacture, and will then show how it can be used in our simplified technique for the capture and analysis of birefringent specimens between crossed polars.

Substantially Non-Birefringent Film

Figure 1:
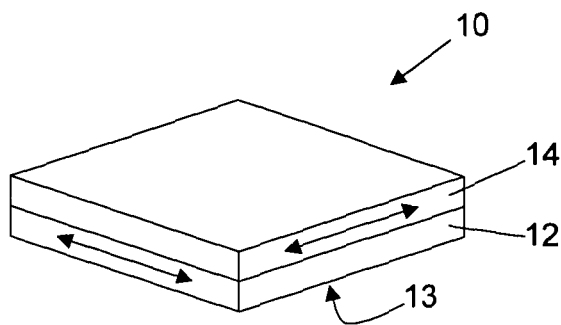
FIG. 1 illustrates a polymer laminate film comprising two layers of polymer tape stuck on top of each other.
Figure 2:
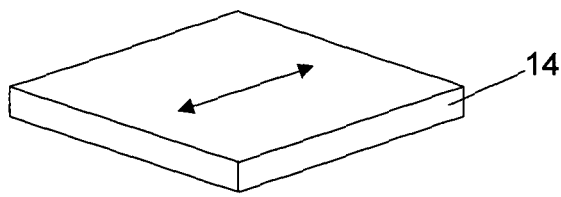
FIG. 2 is an exploded view of the film of FIG. 1.
Figure 2:
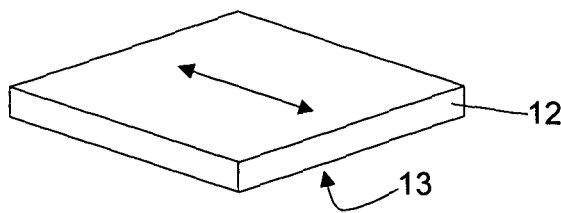

An embodiment of our new substantially non-birefringent film is illustrated in FIG. 1. The film 10 comprises two layers of adhesive transparent polymer tape 12, 14 that, individually, are birefringent. Each layer of adhesive tape 12, 14 may be cut from a conventional roll of adhesive tape. To form the substantially non-birefringent film 10, the two layers 12, 14 are stuck on top of each other to form a laminate structure, with the layers mutually oriented such that the birefringent properties of the two tapes 12, 14 cancel each other out. To achieve this, the second tape 14 is oriented at substantially 90° relative to the first tape 12 (as illustrated by the double-headed arrows in FIG. 1 which denote the orientation of each layer of tape, corresponding to the "long" direction of the roll from which each layer is taken). FIG. 2 illustrates the two layers 12, 14 in exploded form. As those skilled in the art will appreciate, the two layers 12, 14 are made of the same material and are of the same thickness, so that their birefringent properties cancel each other out.

Other layers, coatings or surface treatments may be added either side of the film 10, or between layers 12 and 14, provided the added material does not substantially affect the substantially non-birefringent nature of the film 10.

The film 10 has a wide range of potential applications, not only in forensic science and other fields of scientific or technological research, but also in industrial applications such as optical devices.

Fabrication Technique for the Substantially Non-Birefringent Film

Figure 3:
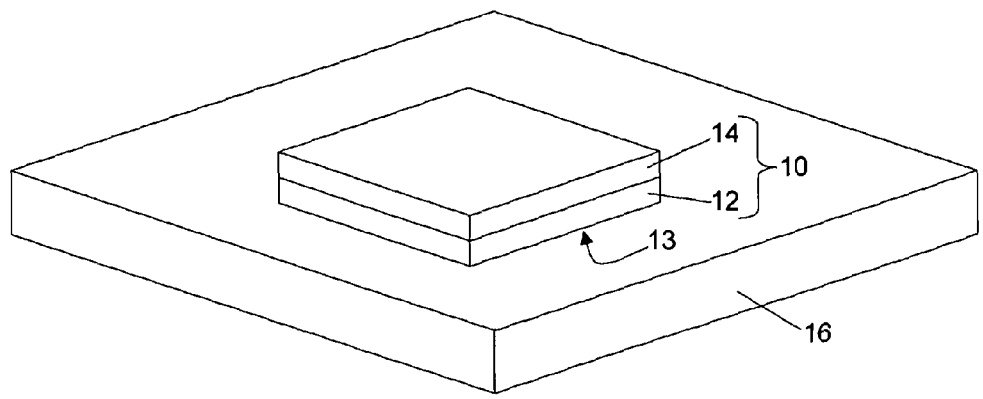
FIG. 3 illustrates the film of FIG. 1 on a glass slide, during manufacture.

With reference to FIG. 3, a piece of substantially non-birefringent polymer film 10 may be made using the following method:

Set up a light source with crossed polars. This may be done by placing two pieces of Polaroid® on top of one another on top of a light box. Once the light box is lit, rotate the upper piece of Polaroid until the polars are crossed (indicated by the lack of light passing therethrough).

Place a piece of glass 16 (or optically similar material) in between the crossed polars (e.g. the two pieces of Polaroid). Stick a first piece of adhesive transparent polymer tape (e.g. Scotch® tape) 12 onto the glass 16.

When the glass 16 is rotated about a vertical axis (i.e. an axis that is essentially perpendicular to the plane of the glass 16), interference colours of varying intensity should be observed in the tape. Rotate the glass 16 to a position at which these colours are at their most intense. Take a second piece of adhesive transparent polymer tape 14 and rotate this, about a vertical axis, above the surface of the glass until the birefringent properties of the two tapes 12, 14 cancel each other out and compensation black is observed through the two pieces of tape. In this position, stick the second piece of tape 14 on top of the first, to form a piece of substantially non-birefringent film 10.

The area where the two pieces of tape 12, 14 overlap is now substantially non-birefringent.

The film 10 may then be removed from the glass 16, as and when required, in order to collect specimens, fibre evidence from a crime scene, etc. The adhesive underside 13 of the first tape layer 12 (that was attached to the glass 16) may be used to pick up the specimens or evidence. The use of the film 10 to collect and examine specimens or evidence will be discussed in more detail below.

For larger-scale manufacture of the film 10, and to facilitate removal of the film from the glass without risking contamination of the adhesive underside 13 of the first tape layer 12, the above method may be adapted as follows:

Before sticking the first piece of tape 12 down, place a piece of backing paper (e.g. from sticky back plastic) or release paper/film on top of the glass 16 and underneath the tape 12. Place the first piece of tape 12 on top of this backing paper. Then, when rotating the second piece of tape 14 above the first piece 12, observe the area around the backing paper for compensation black.

Figure 4:
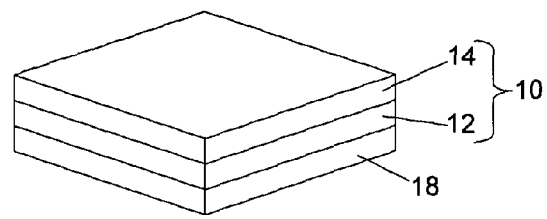
FIG. 4 illustrates the film of FIG. 1 with a piece of backing paper attached.

With reference to FIG. 4, once the two pieces of tape 12, 14 have been stuck together to form a region of substantially non-birefringent film 10, use a scalpel to cut around the outside of the backing paper, to cut out a region of film 10 with backing paper 18 attached. The film 10 can now be easily lifted away from the glass, and can be transported without fear of the contaminating the adhesive underside 13 of the first piece of tape 12.

Once the time comes for the film 10 to be used, the backing paper 18 may be peeled off from the adhesive underside 13 of the first tape layer 12, to enable the adhesive underside 13 to be used to pick up a specimen or evidence.

Examples of Suitable Adhesive Transparent Polymer Tapes

The following films or tapes, which have an adhesive surface on one side, have been identified as being appropriate for use as the first and second tape layers 12, 14. Product numbers are given where possible.

Permacel J-LAR® 'Clear to the Core' tape, model number 96106 as supplied by www.csiequipment.com*

3M 483 tape by Scotch®, model number 97053, as supplied by www.csiequipment.com*

Scotch® Packing Packaging Tape Clear, product number KT000009458*

Remco Latent Print Tape, product number 96101 as supplied by www.csiequipment.com*

Works Essentials Clear Tape*, as supplied from The Works retail chain

Scotch® Book Tape, product number 623929*

Scotch® 3M Decorate and Repair tape*

3 L Tape from Self Laminating Cards, product number 11051*

TESA Crystal Clear adhesive tape, product number 57807*

TESA Office Film Transparent Clear Self-Adhesive Tape, product number 57405-2-0*

Scotch® Easy Use Clear Tape, product number 2533FP6*

Scotch® Crystal Tape, product number FT510030602*

Banner Cellulose tape, product code number 931-0018*

Banner Easy Tear Tape, product number 9310037

Sellotape® Crystal Clear tape

Sellotape® Original Clear Cellulose, product code 503870

Cedars Quick Start Tape

We found those tapes marked with a * above to be particularly good for use with this technique, whereas those tapes without a * are adequate. We also found the Remco Latent Print tape to be sufficiently non-birefringent as to allow analysis of birefringent specimens without needing to layer two pieces of tape together.

Simplified Technique for the Capture and Analysis of Specimens

Figure 5:
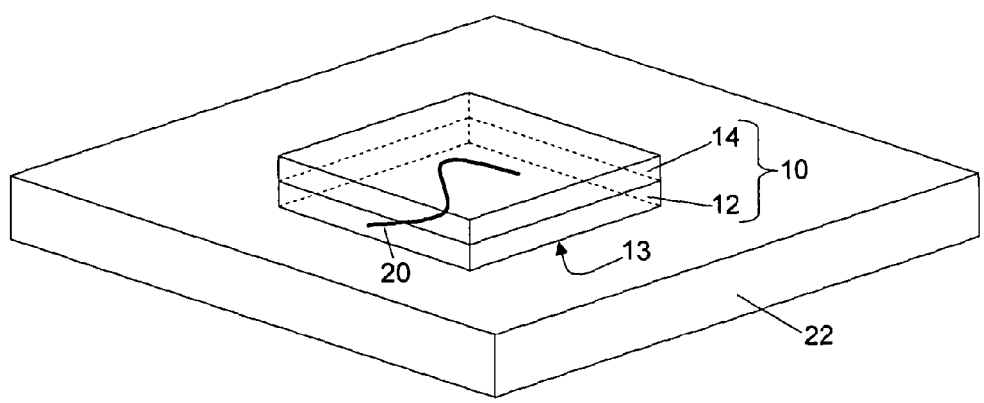
FIG. 5 illustrates the film of FIG. 1 in use, with a piece of fibre evidence captured on the underside of the film, and mounted on a glass slide.

With reference to FIG. 5, using a piece of substantially non-birefringent polymer film 10 as discussed above, a specimen or piece of evidence 20 may be collected using the adhesive underside 13 of the first tape layer 12, using a tape-lift technique (for example as set out below), taking care to avoid contamination of the adhesive underside or the specimen/evidence. The film 10, with the specimen/evidence 20 attached to the adhesive underside 13, may then be attached (using the adhesive underside 13) to another substantially non-birefringent substrate, such as a glass microscope slide 22, for examination between crossed polars.

The following tape-lift technique may be followed to collect fibres at a crime scene, using the substantially non-birefringent film 10:

1. Remove a piece of film 10 from its backing paper 18 using a tab provided.
2. Collect fibres (e.g. fibre 20) using the sticky underside 13 of the film 10.
3. Apply the sticky underside 13 of the film 10 (with the fibres attached) to one face of a microscope slide 22.
4. Put the microscope slide 22, with the film 10 and fibres attached, in a suitable protective box, and package the box in an evidence bag.

The substantially non-birefringent nature of the film 10, and that of the glass slide 22, mean that a birefringent specimen or piece of evidence 20 will be readily visible when viewed between crossed polars, with the surrounding film 10 and glass slide 22 appearing dark. Thus, using this technique, there is no need for the specimen or evidence 20 to be removed from the film 10, and no need for any further preparation of the film 10, slide 22, or specimen/evidence 20. Compared to the prior art technique involving dissection, removal and remounting of the specimen/evidence, it will be appreciated that the present technique greatly simplifies and facilitates the collection and examination procedure, and reduces the risk of contaminating or losing the specimen/evidence.

In an alternative technique, the two layers 12, 14 of the substantially non-birefringent film 10 may be peeled partly apart (to form a Y-shape), and the specimen or evidence may be collected using the adhesive underside of the second tape layer 14 that is normally inside the film. The layers 12, 14 may then be closed together again, thereby retaining the specimen or evidence within the film 10. This has the advantage that the film 10 may then be viewed between crossed polars without attaching it to a glass slide.

For completeness, it should be noted that there are materials (e.g. DNA) that the film 10 is able to collect that cannot be analysed by polarized light microscopy but which could be analysed by other methods. Indeed, a single tape lift could collect both fibre and DNA evidence. Thus, if desired, the film 10 may subsequently be separated from the substrate/slide 22, or (in the alternative technique) the two layers 12, 14 of the film 10 may be separated, in order to remove one or more specimens or pieces of evidence for further analysis.

Further Modifications

We have found that applying a coating of gelatine to the surface of the glass slide 22 onto which the film 10 is to be attached can improve the imaging of the specimen/evidence 20 between crossed polars, since the gelatine causes fewer air bubbles to form between the film 10 and the slide 22. Additionally, or alternatively, the glass slide 22 with film 10 and specimen/evidence 20 attached (with or without a gelatine coating on the slide) may be subjected to relatively gentle heat and pressure, prior to examining between crossed polars, in order to improve the seal between the glass slide 22 and the film 10. These two modifications will now be described in more detail.

Gelatine-Coated Glass Slides

When a piece of film 10 (with specimen/evidence 20) is attached to a conventional glass microscope slide 22, air bubbles are prone to form between the film 10 and slide 22, which impedes the imaging of the specimen/evidence 20 between crossed polars. We have found that applying a coating of gelatine to the glass slide helps to reduce the formation of air bubbles and thus improves the imaging of the specimen/evidence 20 between crossed polars.

Figure 6:
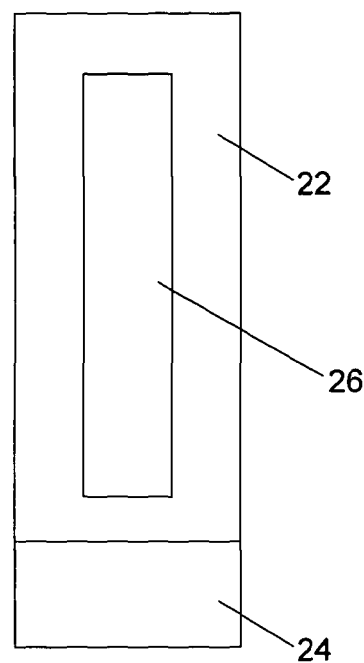
FIG. 6 illustrates a glass slide having a strip of gelatine and a label mounted thereon.

With reference to FIG. 6, the following technique may be used to produce gelatine-covered glass slides:

Take a glass microscope slide 22 and place a piece of sticky label 24 (approximately 3 cm×2.5 cm in size) along one of the shorter edges. Place a strip of gelatine 26 (approximately 2 cm×4 cm in size) in the centre of the slide 22, above the label 24.

Place the slide gelatine side down onto a piece of backing paper (e.g. from some sticky back plastic).

Wrap the slide and backing paper in a folded piece of paper, and pass through a conventional office laminating machine (without a laminating pocket) in order to apply relatively gentle heat and pressure. (Other functionally-equivalent means for applying heat and pressure may alternatively be used.) When the folded piece of paper comes out the other side, leave the slide and backing paper wrapped inside, and roll over the slide with a rolling pin or such like. Then send the slide (still wrapped in the folded piece of paper) back through the laminator. When it comes out the other side, gently place the whole thing underneath a weight (with the weight spread evenly across the whole thing) until the gelatine sets.

Remove the slide and the backing paper from the folded piece of paper. With a blunt scalpel, gently cut away the excess gelatine from around the slide, and cut away the excess backing paper.

Do not separate the slide from the backing paper at this stage.

The backing paper may be removed from the slide 22 at a later stage, as and when it is desired to attach a piece of film 10 with specimen/evidence 20 onto the slide 22.

The gelatine material we used was cut from the sticky side of a clear fingerprint Gel Lifter supplied by Crime Scene Investigation Equipment Ltd. of Media House, 31 Freehold Street, Northampton, NN2 6EW, UK. Alternatively, gelatine material can be made to a suitable consistency by mixing 1 g/ml of gelatine and water. Any gelatine powder can be used, for example, gelatine supplied by Oxoid Ltd, Basingstoke, Hampshire, England.

Instead of gelatine, other materials having similar optical and viscous properties to gelatine may be used to coat the glass slides.

Using a gelatine-coated glass slide, the following modified tape-lift technique may be used to collect fibres at a crime scene, using the substantially non-birefringent film 10 and referring again to FIG. 5:

1. Remove a piece of film 10 from its backing paper 18 using a tab provided.
2. Collect fibres (e.g. fibre 20) using the sticky underside 13 of the film 10.
3. Remove a gelatine-coated microscope slide 22 from a suitably protective box in which it has been stored, and remove its backing paper.
4. Apply the sticky underside 13 of the film 10 (with the fibres attached) to the sticky gelatine-coated side of the microscope slide 22.
5. Put the microscope slide 22 (with the film 10 and fibres attached) back in its box, and package the box in an evidence bag.

Application of Heat and Pressure Prior to Examining Between Crossed Polars

Figure 7:
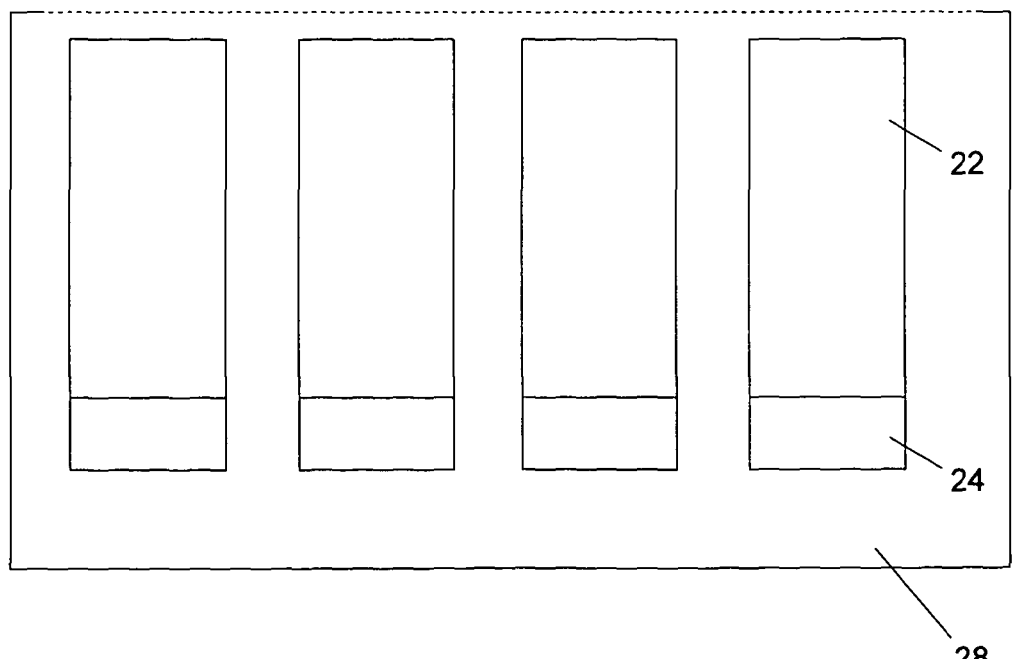
FIG. 7 illustrates four glass slides placed inside a folded piece of paper, for the application of heat and pressure prior to examination.

With reference to FIG. 7, the following method may be carried out with glass slides 22 on which pieces of film 10 with forensic evidence 20 have been attached, prior to examination between crossed polars in a laboratory, in order to improve the seal between each glass slide 22 and film 10.

1. Take the slides carefully out of their evidence bags and slide boxes.
2. Place each slide tape side down on top of some backing paper (e.g. from some sticky back plastic), and place inside a folded piece of paper (e.g. A4 size) as shown in FIG. 7. We suggest no more than four slides per piece of folded A4 paper.
3. Pass the piece of folded paper through a conventional office laminating machine (without a laminating pocket), folded side first, in order to apply relatively gentle heat and pressure.
4. Place an even distributed weight on top of the slides (still within the folded paper), and leave for approximately 10 minutes or until the gelatine (if the slides are gelatine-coated) has set.
5. Remove the slides from the folded paper and examine underneath a microscope as normal.

Instead of using an office laminating machine, other functionally-equivalent means for applying heat and pressure to the slides may alternatively be used.

Test Results

The tables presented in FIGS. 8 and 9 contain data obtained using a tilting compensator that shows the validity of the present work. One set of data (FIG. 8) is based on observations made on a fibre (so-called "Fibre 5") that has a relatively low optical path difference (OPD), whilst the other set (FIG. 9) concerns a fibre (so-called "Fibre 123") that has a moderate OPD. When these observations were made, the fibres concerned were held taught, but not stretched, such that, in each case, the main axis of the fibre was a straight line.

For each fibre, the data is presented as a number of tables. The first column of each of these describes the position of the straight line that is the main axis of the fibre relative to a second straight line that is both across the stage of the microscope and parallel to it. In those tables in which this column is headed "Angle", the data refers to the angle in degrees that was made between these two lines. In order to change that angle from one value to another, the fibre, but not the other materials present on the stage of the microscope or the second line referred to above, was rotated. The axis of this rotation was essentially parallel to the light path of the instrument and essentially perpendicular to both of the straight lines referred to above. In those tables in which the first column is headed "Position", the data merely differentiate between one measurement and the next. Between each such measurement, the fibre was rotated through an unmeasured angle about an axis that was essentially parallel to the light path of the instrument and essentially perpendicular to the straight lines referred to above.

For each table in FIGS. 8 and 9, the important column is the one on the right-hand side. This shows multiple measurements of the OPD, measured in nanometers, of a fibre under the conditions indicated by the title of the table concerned. The important comparisons are the mean and standard deviation (SD) values (see the foot of each table) for the OPD for the fibres observed in Depex (a standard mounting medium, which provides benchmark data), J-LAR® (a conventional tape-lift medium), and observations made using our new tape (corresponding to the film 10 discussed above), and the new tape (i.e. film 10) with gelatine. In each case, whilst the mean and SD data for the new tape (with or without gelatine) do not fully agree with those obtained from Depex, the data is of much higher precision (as expressed by a low SD value) than that produced by the J-LAR®. Furthermore, the mean value for the OPD obtained from fibres examined under the new tape (with or without gelatine) is within the expected range.

Additional Analytical Techniques and Applications with which Embodiments of the Invention may be Used As well as being used for the optical examination of fibres and other samples between crossed polars, the polymer laminate films produced as embodiments of the invention may also be used in other analytical techniques. We have investigated this in the areas of fluorescent microscopy, microspectrophotometry and confocal Raman microspectroscopy, as follows:

1. Fluorescent Microscopy

The tapes mentioned above (under the heading "Examples of suitable adhesive transparent polymer tapes") were analysed for fluorescent properties using a Nikon® Eclipse 50i microscope and Nikon® Intensilight C-HGFI (HG Pre-centered Fiber Illuminator) light source and EPI fluorescence attachments.

Each of the tapes were viewed under two wavelength ranges; 350-420 nm and 440-520 nm. Any fluorescence of the tape was noted.

The following tapes were identified as being either non-fluorescent or exhibited only very low fluorescence:
Permacel J-LAR® 'Clear to the Core' tape
Scotch® Packing Packaging Tape Clear
Works Essentials Clear Tape
Scotch® 3M Decorate and Repair tape
Scotch® Easy Use Clear Tape
Scotch® Crystal Tape
Banner Easy Tear Tape
Sellotape® Crystal Clear tape
Cedars Quick Start Tape
The following tapes showed slight fluorescent properties:
Sellotape® Original Clear Cellulose
TESA Crystal Clear adhesive tape
TESA Office Film Transparent Clear Self-Adhesive Tape
Banner Cellulose tape
3 L Tape from Self Laminating Cards
The following tapes exhibited the most fluorescence:
3M 483 tape by Scotch®
Remco Latent Print Tape
Scotch® Book Tape It is felt that any tapes showing low fluorescence or no fluorescence would easily allow any fluorescent fibres to be identified if they were mounted on (or in) polymer laminate films made using such tapes. Tapes showing some fluorescent properties may cause some interference when analysing the fluorescent properties of fibres. When analysing strongly fluorescent fibres, it would still be possible for the fibres' fluorescent properties to be identified, but weakly fluorescent fibres may not be identified due to the fluorescent qualities of the tape.

2. Microspectrophotometry (MSP) and Confocal Raman Microspectroscopy

Fibre samples were submitted to Contact Traces Ltd (Milton Park, Abingdon OX14 4SA, UK), a specialist provider of forensic microscopy and spectroscopy services, as (a) loose fibres in gripseal polythene bags, and (b) corresponding fibres mounted on polymer laminate films produced as embodiments of the present invention. Some of the fibre samples were certified reference samples provided by Microtrace LLC (Elgin, Ill. 60123, USA). The purpose of the investigation at Contact Traces Ltd was to ascertain whether or not the samples mounted on the laminate films could be analysed by microspectrophotometry (MSP) and confocal Raman microspectroscopy.

It was found that the fibres mounted on the polymer laminate films could be analysed to a satisfactory standard using both these analytical techniques. In the experience of a fibres expert at Contact Traces Ltd, the samples mounted on the laminate films behaved as would be expected for fibres mounted under any clear adhesive tape.

The test procedures and results were as follows:

2.1. Microspectrophotometry (MSP)

The following coloured fibre samples were analysed using a J&M Tidas 200 MSP in the visible range between 380 and 730 nm:
Fibre 67 from Microtrace Reference Set
Fibre 87, from Microtrace Reference Set
Contact Traces Blue Fibre Loose fibres from the samples above were mounted in Entellan® under glass coverslips. Entellan® is a mounting medium which is conventionally used for this technique. MSP spectra generated from the Entellan-mounted samples were compared to those generated from corresponding samples mounted on various polymer laminate films produced as embodiments of the invention.

Figure 10:
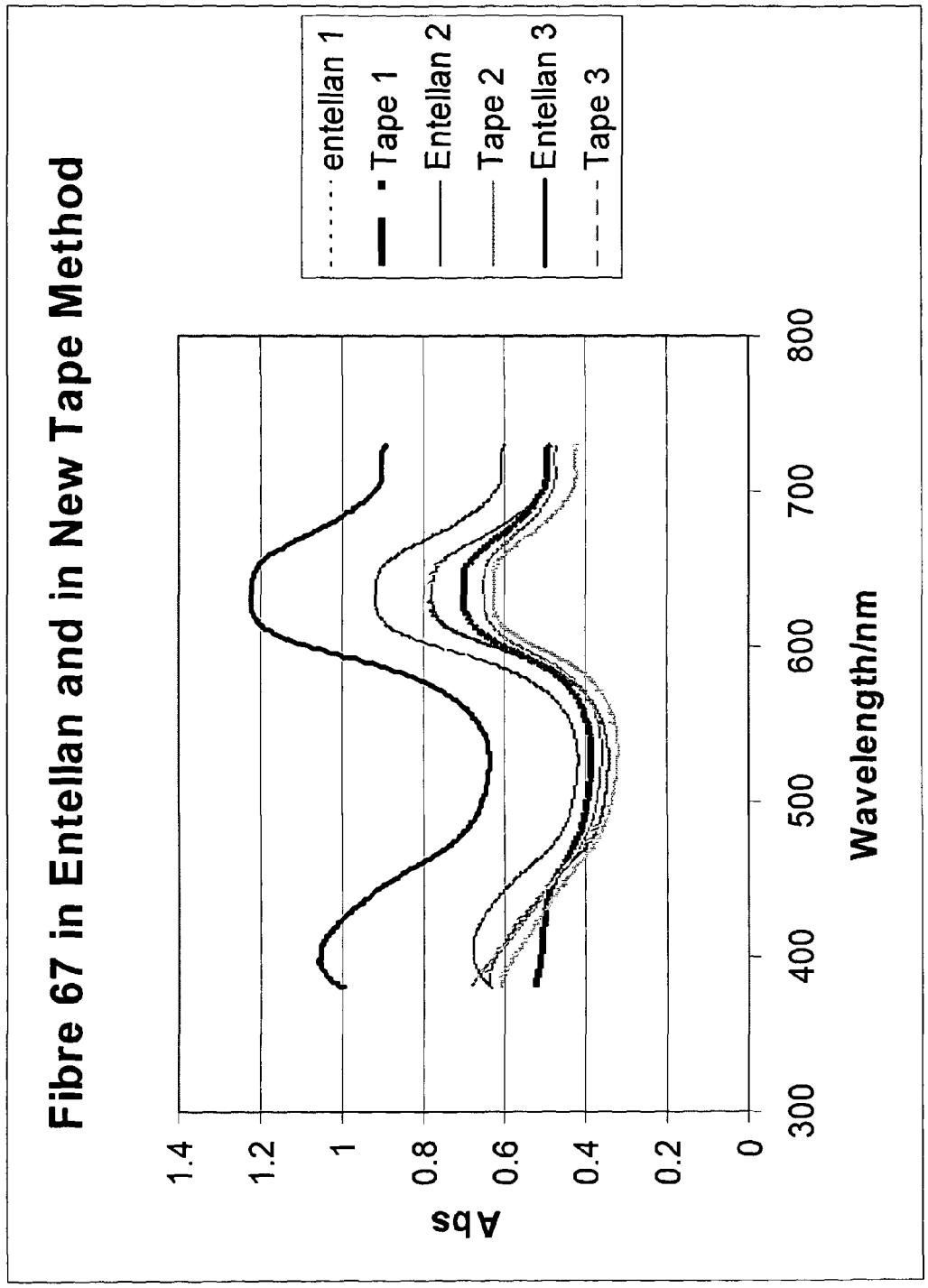
FIGS. 10, 11 and 12 are microspectrophotometry plots of relative absorption against wavelength of light, for fibres mounted on various polymer laminate films produced as embodiments of the invention, or for the same fibres each mounted between a glass slide and cover slip in a conventional "Entellan"® mounting medium.
Figure 11:
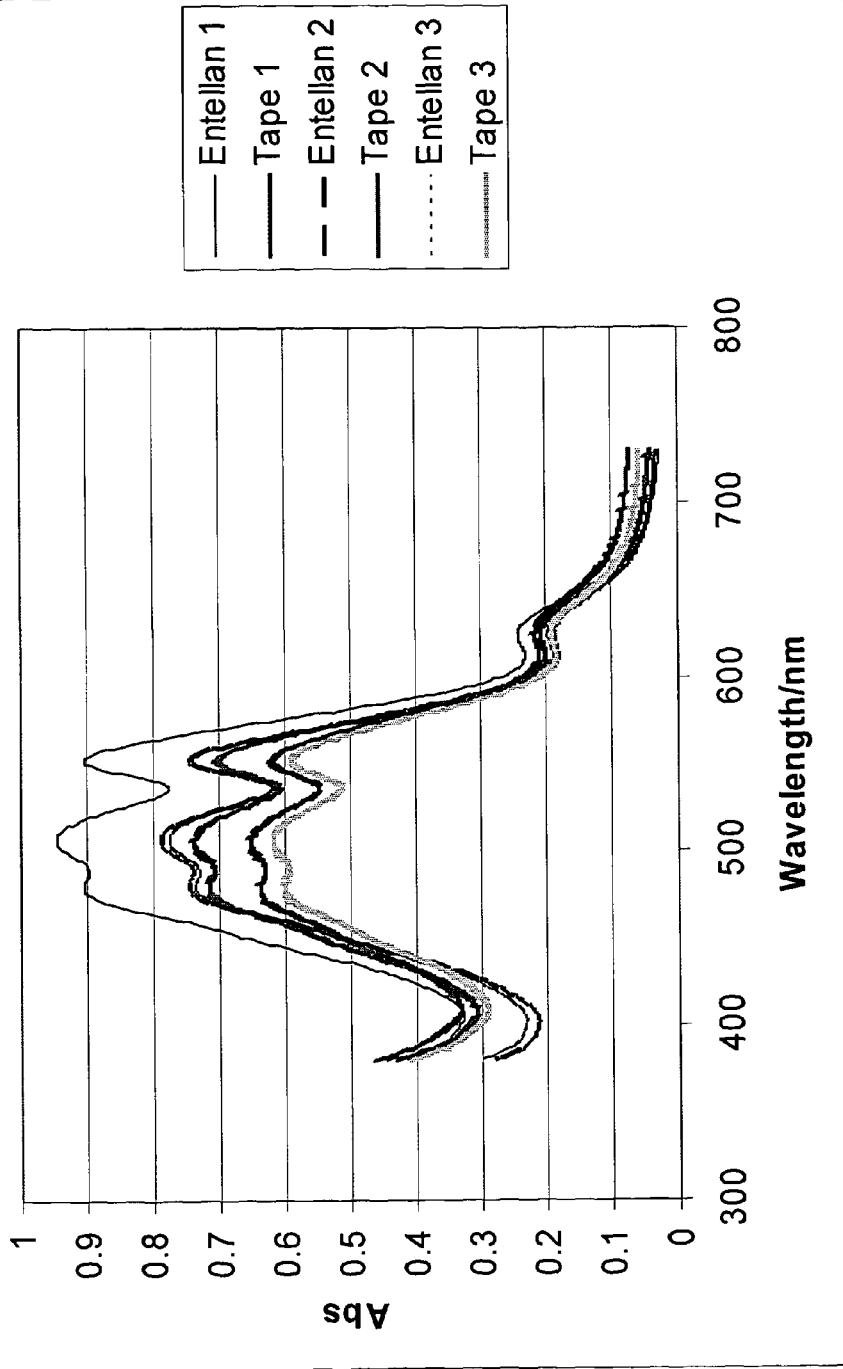
Figure 12:
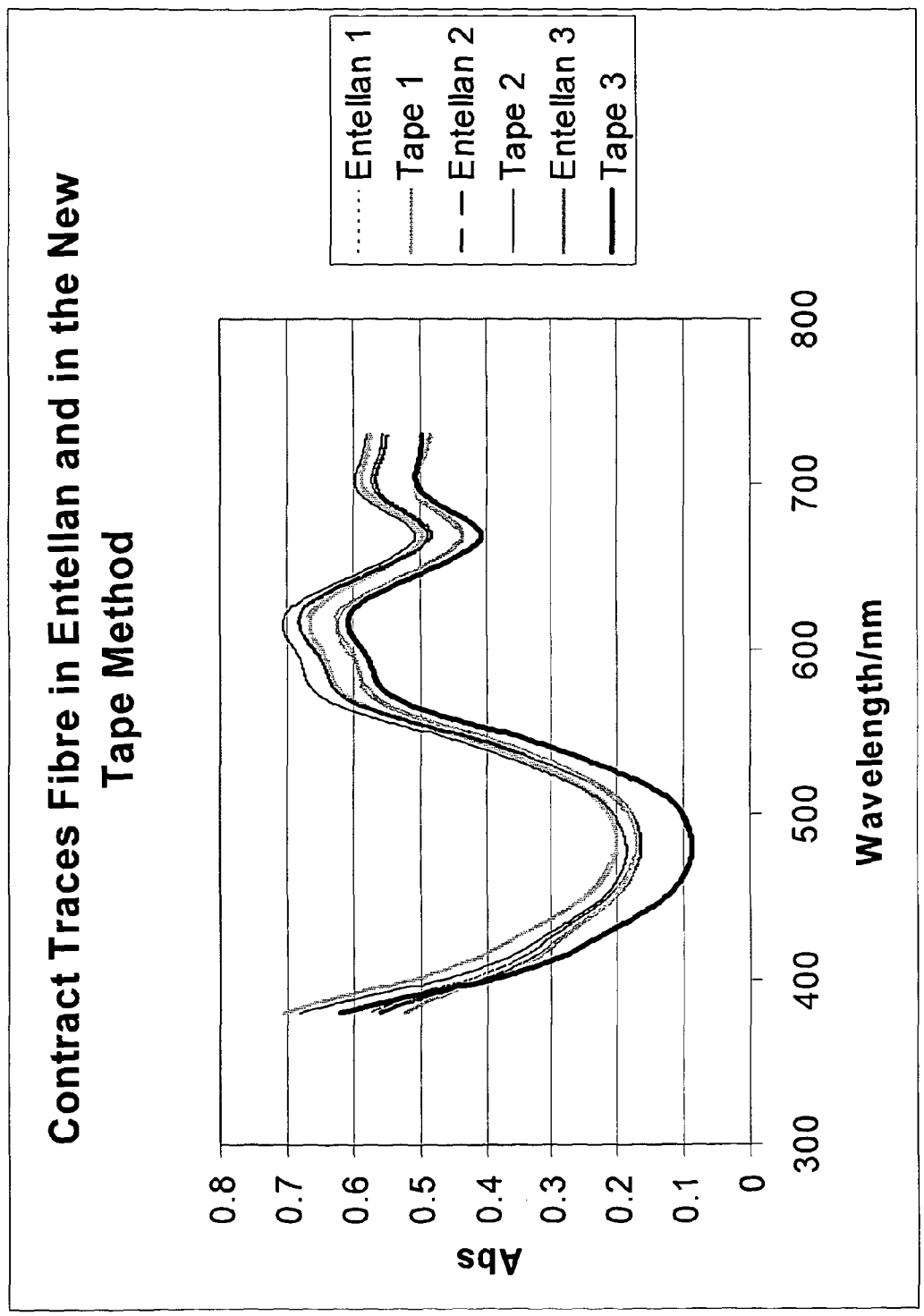

The results are given in FIGS. 10, 11 and 12. FIG. 10 shows the results for the "Fibre 67", FIG. 11 shows the results for the "Fibre 87", and FIG. 12 shows the results for Contact Traces' "Blue Fibre". The lines in the plots for which the key states 'Entellan' are for the samples mounted in the conventional Entellan® mounting medium. The lines in the plots for which the key states 'tape' are for the corresponding fibre samples mounted on polymer laminate films produced as embodiments of the invention.

From these results, it can be seen that the quality of the spectra generated from the fibres mounted on our laminate films is similar to that produced using the standard Entellan® mounting material, and gives no cause for concern.

2.2 Raman Spectroscopy

Figure 13:
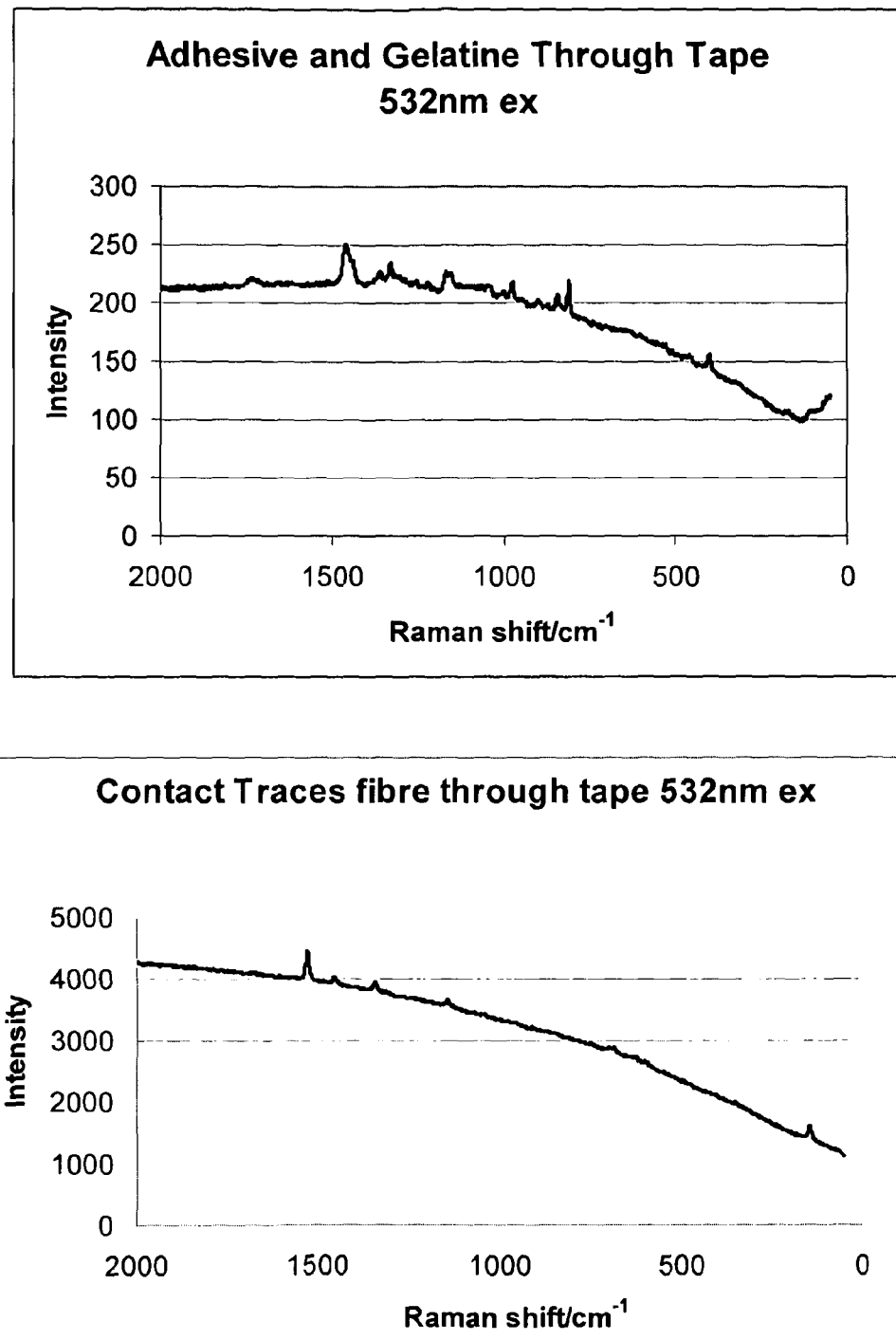
FIG. 13 shows a series of results from Raman spectroscopy tests performed on various fibres mounted on polymer laminate films produced as embodiments of the invention.
Figure 13:
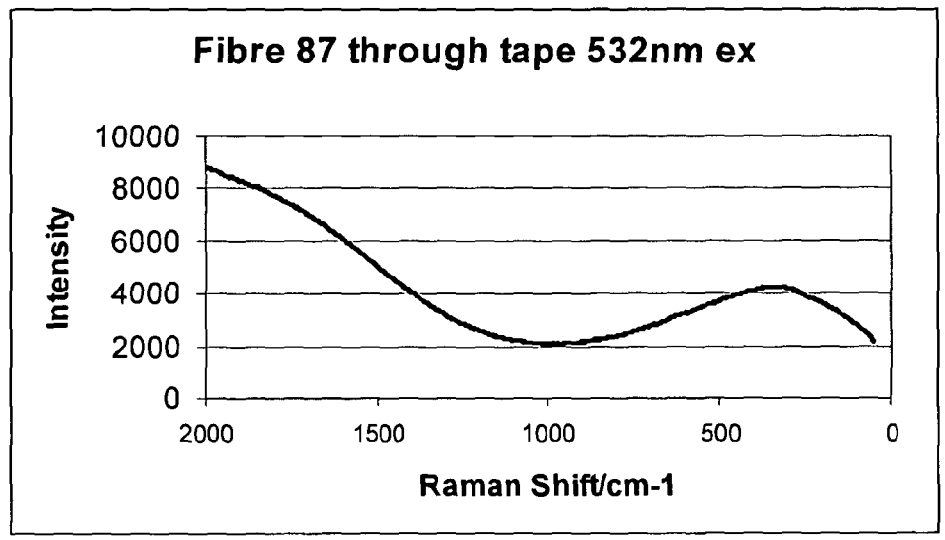
Figure 13:
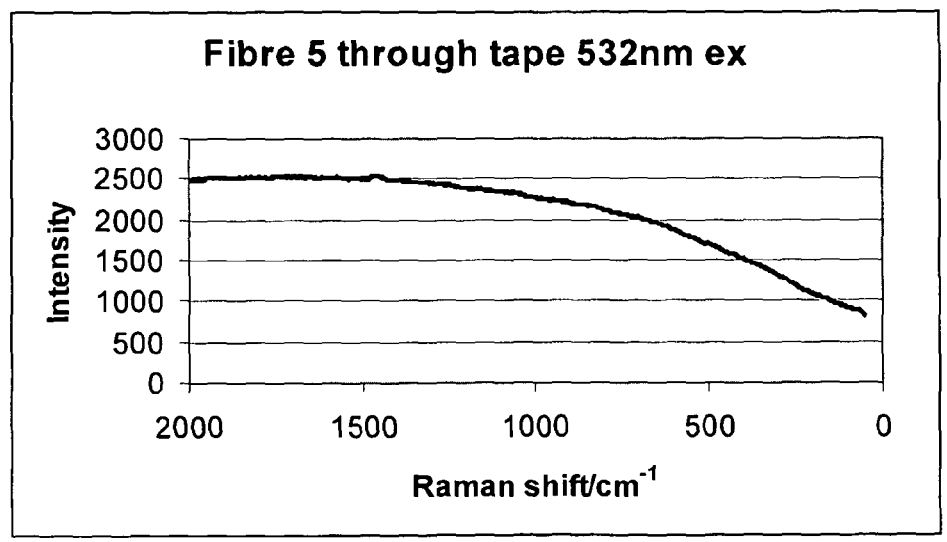
Figure 13:
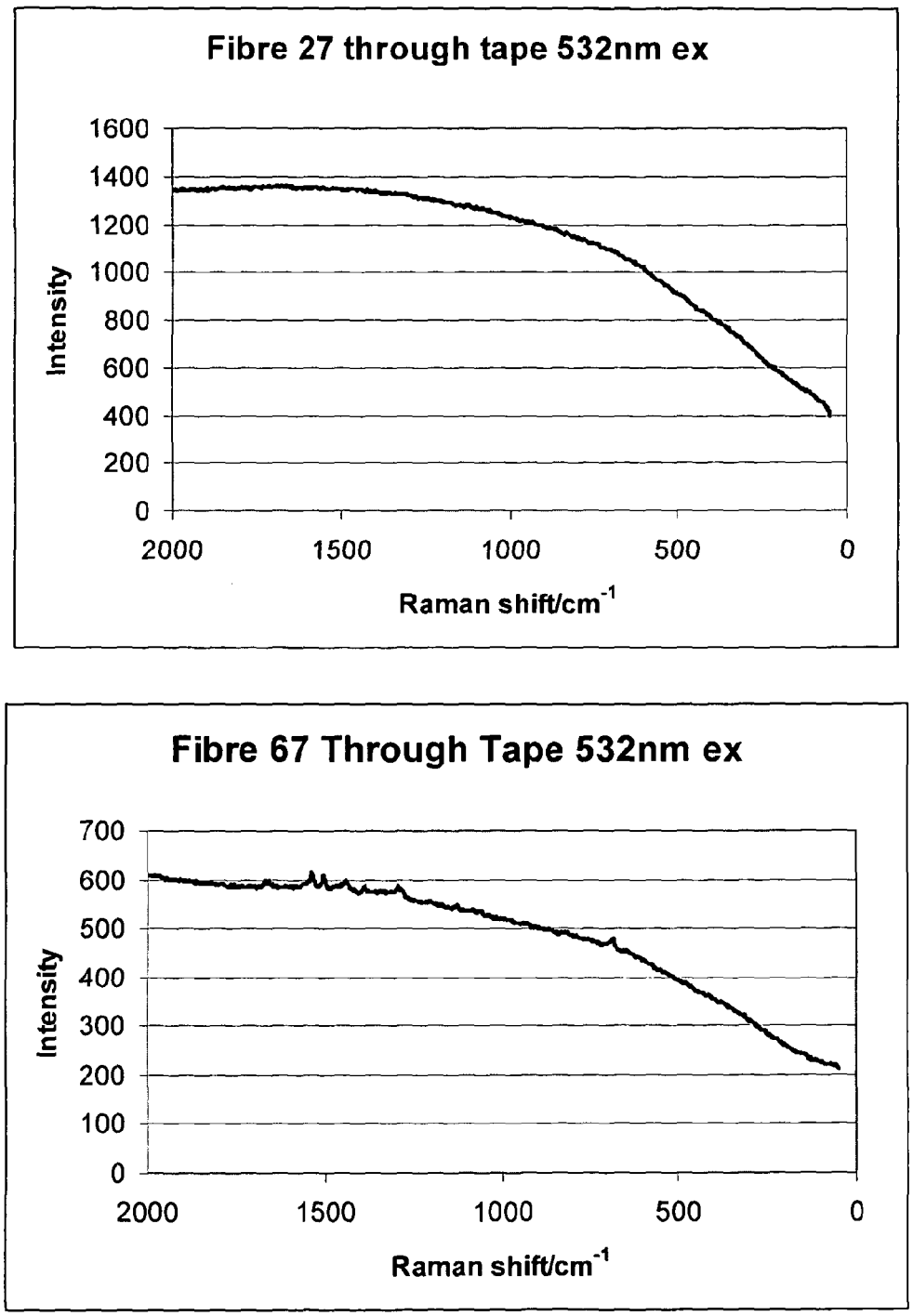
Figure 13:
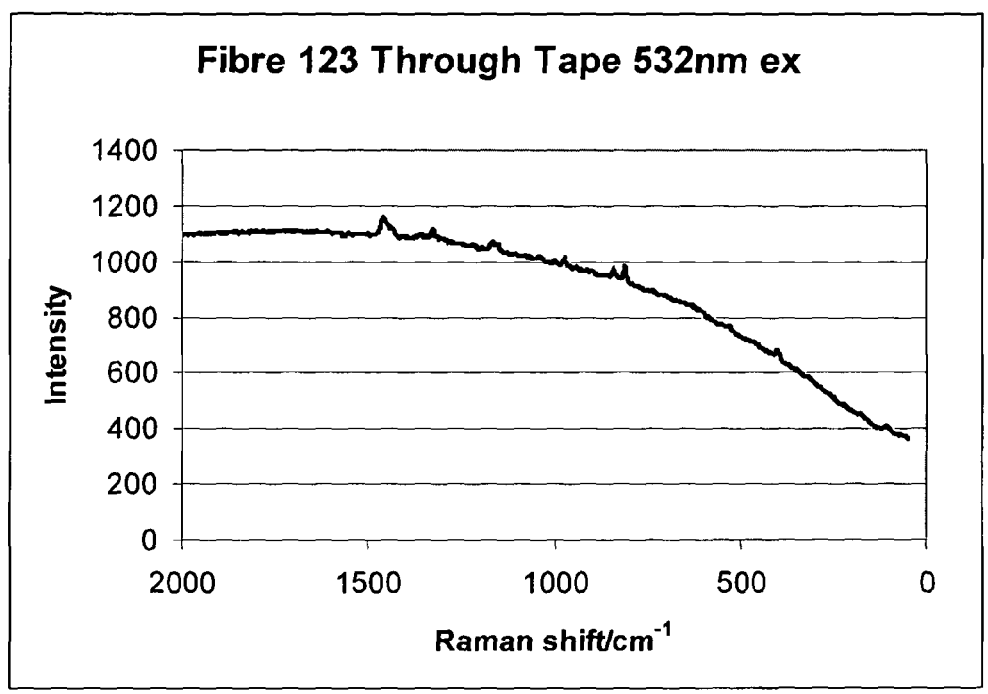

The following tape mounted samples were analysed using a Thermo DXR Raman dispersive microscope using 532 nm (green) laser excitation. Spectra were obtained using an optimized set of conditions that varied for each fibre sample.
Contact Traces Blue Fibre
Fibre 123, from Microtrace Reference Set
Fibre 67, from Microtrace Reference Set
Fibre 5, from Microtrace Reference Set
Fibre 127, from Microtrace Reference Set
Fibre 87, from Microtrace Reference Set The results are given in the series of plots in FIG. 13. Not all of the fibres gave Raman spectra of good quality—however, this was largely due to the colourant fluorescing or the fibre being a weak Raman scatterer, and was not unexpected. The effect of the taping on the quality of the spectrum was negligible and was in keeping with what would be expected from any clear adhesive tape. Pigmented fibres such as the Contact Traces sample, and fibres 87 and 67, provided clear Raman spectra from the pigments. This showed that it was possible to identify the pigments used in fibres mounted on the tapings using this technique.

As an internal validation and where appropriate, spectra from the colourless fibres were searched against in-house spectral databases held by Contact Traces Ltd., and the following matches were obtained:
Fibre 123 matched to polypropylene
Fibre 5 matched to acrylic These search results were as expected, and agree with information on the fibre types provided by Microtrace Ltd. This shows that it is possible to identify colourless fibres at the polymer level using the invention using a confocal Raman technique.

The invention claimed is:

1. A method for optically examining a birefringent specimen, the method comprising the steps of:
   collecting a specimen using a substantially non-birefringent polymer film having an adhesive surface, such that the specimen is attached to the adhesive surface;
   attaching the film to a substantially non-birefringent substrate after collecting the specimen, the substrate having a surface onto which the film is attached, the surface comprising a coating of gelatine, or another material having similar optical and viscous properties to gelatine; and
   examining, between crossed polars, the specimen attached to the said film.

2. A method as claimed in claim 1, wherein the film has an adhesive underside, and the step of collecting the specimen is performed by placing the film onto the specimen such that the adhesive underside contacts the specimen, and then lifting the film up.

3. A method as claimed in claim 1, wherein the film comprises two or more layers, and the step of collecting the specimen is performed by peeling a layer at least partly away so as to expose an adhesive surface, collecting the specimen using the said adhesive surface, and closing the layers together again, so as to seal the specimen between the layers.

4. A method as claimed in claim claim 1, wherein the substrate is a glass slide.

5. A method as claimed in claim 1, further comprising an initial step of removing a layer of backing material from the film prior to collecting the specimen.

6. A method as claimed in claim 1, wherein the substantially non-birefringent film is a laminate film comprising a first birefringent polymer layer and a second birefringent polymer layer, the first and second layers being mutually oriented such that the birefringent properties of the two layers cancel each other out.

7. A method as claimed in claim 1, wherein the specimen is a piece of evidence such as a fibre from a crime scene, and the method is for the forensic analysis of the said evidence.

8. A method for optically examining a birefringent specimen, the method comprising the steps of:
   collecting a specimen using a substantially non-birefringent polymer film having an adhesive surface, such that the specimen is attached to the adhesive surface;
   attaching the film to a substantially non-birefringent substrate after collecting the specimen;
   applying heat and pressure to the substrate, with the film and specimen attached; and
   examining, between crossed polars, the specimen attached to the said film.

9. A method as claimed in claim 8, wherein the application of heat and pressure comprises placing the substrate, with the film and specimen attached, between two layers of paper, and passing it through a laminating machine.

10. A method as claimed in claim 9, further comprising placing a weight on the substrate, with the film and specimen attached, after it has passed through the laminating machine.

* * * * *